(12) United States Patent
Van Benthem et al.

(10) Patent No.: US 7,678,876 B2
(45) Date of Patent: Mar. 16, 2010

(54) HYDROXY-AROMATIC COMPOUND, PROCESS FOR THE PREPARATION THEREOF, AND USE OF THE COMPOUND

(75) Inventors: Rudolfus A T M Van Benthem, Limbricht (NL); Renier H M Kierkels, Beegden (NL)

(73) Assignee: DSM IP Assets B.V., Heerlen (NL)

( * ) Notice: Subject to any disclaimer, the term of this patent is extended or adjusted under 35 U.S.C. 154(b) by 134 days.

(21) Appl. No.: 11/791,847

(22) PCT Filed: Dec. 1, 2005

(86) PCT No.: PCT/NL2005/000826

§ 371 (c)(1),
(2), (4) Date: May 30, 2007

(87) PCT Pub. No.: WO2006/059903

PCT Pub. Date: Jun. 8, 2006

(65) Prior Publication Data
US 2008/0194790 A1    Aug. 14, 2008

(30) Foreign Application Priority Data
Dec. 2, 2004    (EP) .................................. 04078281
Mar. 1, 2005    (EP) .................................. 05075496

(51) Int. Cl.
*C08G 63/06*    (2006.01)
*C08G 65/38*    (2006.01)

(52) U.S. Cl. ........................ 528/206; 528/212; 528/219; 568/733; 568/734; 568/739

(58) Field of Classification Search ................ 528/206, 528/212, 219; 568/733, 734, 739
See application file for complete search history.

(56) References Cited

U.S. PATENT DOCUMENTS

| | | | |
|---|---|---|---|
| 3,450,746 A | 6/1969 | Stapfer | |
| 3,639,447 A | 2/1972 | Taylor et al. | |
| 4,007,282 A | 2/1977 | Mauz et al. | |
| 4,178,466 A | 12/1979 | Gardner et al. | |
| 4,229,382 A | 10/1980 | Mayer et al. | |
| 4,358,624 A | 11/1982 | Mark et al. | |
| 4,365,098 A | 12/1982 | Mark et al. | |
| 4,465,765 A | 8/1984 | Leppard et al. | |
| 4,837,293 A | 6/1989 | Silvis et al. | |
| 4,888,444 A | 12/1989 | Ravichandran et al. | |
| 5,674,482 A | 10/1997 | Regan et al. | |

FOREIGN PATENT DOCUMENTS

| | | |
|---|---|---|
| AT | 141 159 B | 3/1935 |
| DE | 193 634 | 12/1906 |
| DE | 872 045 | 3/1953 |
| DE | 30 29 026 A1 | 2/1982 |
| EP | 1 125 908 A1 | 8/2001 |
| FR | 4823 M | 2/1969 |
| FR | 6857 M | 4/1969 |
| FR | 1579608 | 8/1969 |
| GB | 1 574 944 | 9/1980 |
| JP | 63-188647 | 12/1988 |
| JP | 1-203343 | 8/1989 |
| JP | 4-27243 | 9/1992 |
| JP | 5-197151 | 8/1993 |
| JP | 6-172257 | 6/1994 |
| JP | 8-211600 | 8/1996 |
| WO | WO 00/55123 | 9/2000 |
| WO | WO 2004/026807 A1 | 4/2004 |

OTHER PUBLICATIONS

Gong et al, "Regioselective Substitution of Phenols with Trifluoroacetaldehyde Ethyl Hemiacetal," Bull. Chem. Soc. Jpn, vol. 74, 2001, pp. 377-383.
Tinapp P, "Herstellung von Mandelalehyden durch katalytische Hydrierung von Mandelsäurenitrilen mit Raney-Nickel in Gegenwart von Schwefelsäure," Chemische Berichte, Verlag Chemie GMBH, Weinhem, DE, vol. 104, No. 7, 1971, pp. 2266-2272.
Gong et al, "Facile Substitution of N,N-Dimethylanilines and Phenols with Trifluoroacetaldehyde Ethyl Hemiacetal," Synlett, Thieme International, Stuttgart, DE, No. 9, 1999, pp. 1403-1404.

(Continued)

*Primary Examiner*—Terressa M Boykin
(74) *Attorney, Agent, or Firm*—Nixon & Vanderhye P.C.

(57) ABSTRACT

Hydroxy-aromatic compounds of formula (I) are provided:

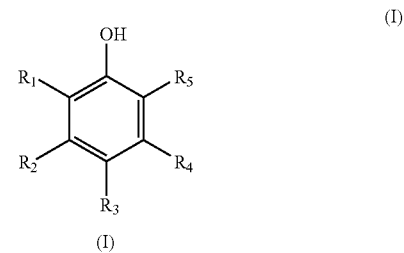

(I)

Figure 1:
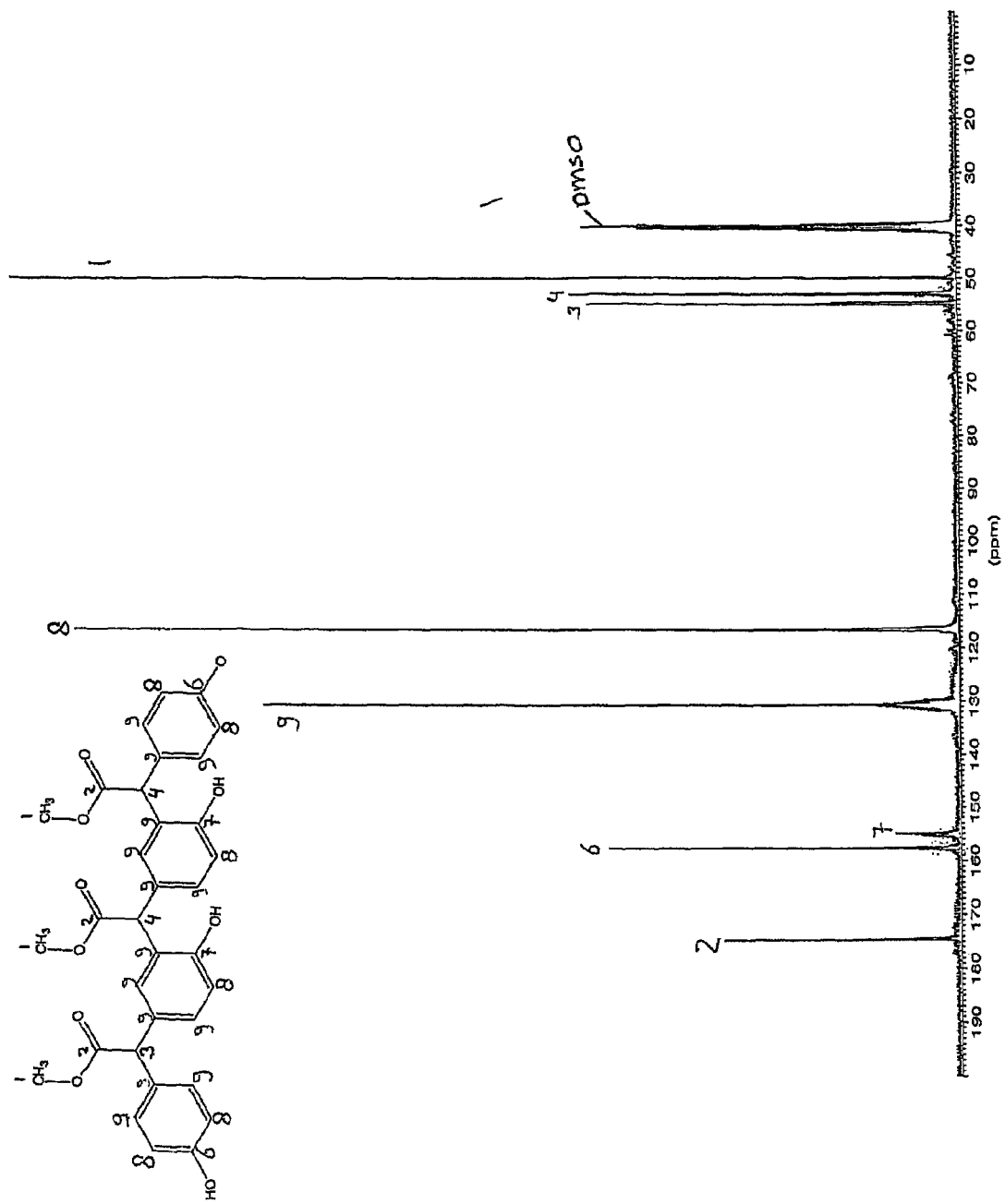

wherein at least one of the set consisting of $R_1$, $R_3$, and $R_5$ is a group of formula (II); any remaining one or two of the set consisting of $R_1$, $R_3$, and $R_5$ being H, OH, a $C_1$-$C_{12}$ alkyl group or an oligomeric or polymeric system; $R_2$ and $R_4$ are H, OH, a $C_1$-$C_{12}$ alkyl group or an oligomeric or polymeric system;
wherein formula (II) is the following group:

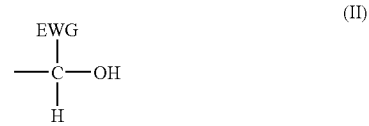

wherein EWG is an electron-withdrawing group.

11 Claims, 2 Drawing Sheets

OTHER PUBLICATIONS

Casiraghi et al, "Selectivity in Reactions between Metal Phenolates and Trichloroacetaldehyde; A Mild Synthesis of 2-(2,2,2-Trichloro-1-hydroxyethyl)phenols," Synthesis, Georg Thieme Verlag, Stuttgart, DE, 1979, pp. 824-825.

Ladenberg et al, "The Synthesis of 3-Hydrox-2-(3)-benzofuranone and of 4-Hydroxymandelic Acid," Journal of the American Chemical Society, American Chemical Society, Washington, DC, US, vol. 58, 1936, pp. 1292-1294.

Shirai et al, "Electrochemical oxidation of 2,2,2-trifluoroethanol to trifluoroacetaldehyde 2,2,2-trifluoroethyl hemiacetal," Tetrahedron Letters, Elsevier, Amsterdam, NL, vol. 41, No. 31, Jul. 29, 2000, pp. 5873-5876.

Cativiela et al, "The replacement of mineral acids by sulfonic resins in the synthesis of rac-5-(4-hydroxyphenyl)hydantoin from p-hydroxymandelic acid and urea—Comparison of alternative methods," Applied Catalysis A: General, Elsevier Science, Amsterdam, NL, vol. 274, No. 1-2, Oct. 28, 2004, pp. 9-14.

Database Caplus, Chemical Abstracts Service, Columbus, Ohio, US; Takashima, Masanobu et al, "Recording Material," XP 002362757 & JP 62 060686 A2, Mar. 17, 1987.

Database Caplus, Chemical Abstracts Service, Columbus, Ohio, US; Ikwakura, Ken et al, "Selective esterification of alcoholic hydroxy group-containing phenols," XP 002362758 & JP 04 257543 A2, Sep. 11, 1992.

Database Caplus, Chemical Abstracts Service, Columbus, Ohio, US; Itonaga, Yasuhiro et al, "Preparation of tetrakisphenols from phenols or benzenediols via bisphenol monoaldehydes," XP 002362759 & JP 2004 277358 A2, Oct. 7, 2004.

Database Caplus, Chemical Abstracts Service, Columbus, Ohio, US; Brzozowski, Zbigniew et al, "Chlorobis(phenols)," XP 002362760 & PL 86 401 P, May 31, 1976.

Database Beilstein, Beilstein Institut zur Förderung der Chemischen Wissenschaft, Frankfurt am, Main, DE; XP002362761 & Can. J. Chem., vol. 64, 1986, pp. 932-935.

Database Beilstein, Beilstein Institut zur Förderung der Chemischen Wissenschaft, Frankfurt am, Main, DE; XP002362762 & J. Org. Chem., vol. 26, 1961, pp. 1420-1422.

Database Beilstein, Beilstein Institut zur Förderung der Chemischen Wissenschaft, Frankfurt am, Main, DE; XP002362763 & J. Org. Chem., vol. 27, 1962, pp. 3092-3095.

Database Beilstein, Beilstein Institut zur Förderung der Chemischen Wissenschaft, Frankfurt am, Main, DE; XP002362764 & Russ. J. Org. Chem. vol. 31, No. 1.1, 1995, pp. 61-63.

Database Beilstein, Beilstein Institut zur Förderung der Chemischen Wissenschaft, Frankfurt am, Main, DE; XP002362765 & Collect. Czech. Chem. Commun., vol. 66, No. 8, 2001, pp. 1250-1256.

Database Beilstein, Beilstein Institut zur Förderung der Chemischen Wissenschaft, Frankfurt am, Main, DE; XP002362766 & J. Chem. Soc., 1928, p. 2226.

Database Beilstein, Beilstein Institut zur Förderung der Chemischen Wissenschaft, Frankfurt am, Main, DE; XP002362767 & Org Prep. Proced. Int., vol. 33, No. 1, 2001, pp. 95-100.

Database Beilstein, Beilstein Institut zur Förderung der Chemischen Wissenschaft, Frankfurt am, Main, DE; XP002362768 & Arch. Pharm., vol. 292, 1959, pp. 690-695.

Database Beilstein, Beilstein Institut zur Förderung der Chemischen Wissenschaft, Frankfurt am, Main, DE; XP002362769 & Helv. Chim. Acta, vol. 43, 1960, pp. 1086-1112.

Database Beilstein, Beilstein Institut zur Förderung der Chemischen Wissenschaft, Frankfurt am, Main, DE; XP002362770 & Chem. Pharm. Bull., vol. 51, No. 11, 2003, pp. 1325-1327.

Database Beilstein, Beilstein Institut zur Förderung der Chemischen Wissenschaft, Frankfurt am, Main, DE; XP002362771 & J. Am. Chem. Soc., vol. 45, 1923, p. 1062.

Database Beilstein, Beilstein Institut zur Förderung der Chemischen Wissenschaft, Frankfurt am, Main, DE; XP002362772 & J. Am. Chem. Soc., vol. 112, No. 22, 1990, pp. 7861-7868.

Database Beilstein, Beilstein Institut zur Förderung der Chemischen Wissenschaft, Frankfurt am, Main, DE; XP002362773 & J. Chem. Soc., 1955, pp. 3914-3918.

Database Beilstein, Beilstein Institut zur Förderung der Chemischen Wissenschaft, Frankfurt am, Main, DE; XP002362774 & Bull. Acad. Sci. USSR Div. Chem. Sci., 1968, p. 863.

Database Beilstein, Beilstein Institut zur Förderung der Chemischen Wissenschaft, Frankfurt am, Main, DE; XP002362775 & J. Org. Chem., vol. 22, 1957, pp. 1439-1442.

Database Beilstein, Beilstein Institut zur Förderung der Chemischen Wissenschaft, Frankfurt am, Main, DE; XP002360790 & Tetrahedron, vol. 39, No. 13, 1983, pp. 2147-2150.

Database Beilstein, Beilstein Institut zur Förderung der Chemischen Wissenschaft, Frankfurt am, Main, DE; XP002360791 & Bull. Soc. Chim. Fr., 1979, pp. 583-591.

Database Beilstein, Beilstein Institut zur Förderung der Chemischen Wissenschaft, Frankfurt am, Main, DE; XP002360792 & Chem. Commun., vol. 17, 2002, pp. 1914-1915.

Database Beilstein, Beilstein Institut zur Förderung der Chemischen Wissenschaft, Frankfurt am, Main, DE; XP002360793 & Eur. J. Org. Chem., vol. 12, 2002, pp. 1984-1988.

Database Beilstein, Beilstein Institut zur Förderung der Chemischen Wissenschaft, Frankfurt am, Main, DE; XP002360794 & Liebigs Ann. Chem., vol. 313, 1990, p. 87.

Database Beilstein, Beilstein Institut zur Förderung der Chemischen Wissenschaft, Frankfurt am, Main, DE; XP002360795 & J. Chem. Soc., 1959, pp. 257-262.

Database Beilstein, Beilstein Institut zur Förderung der Chemischen Wissenschaft, Frankfurt am, Main, DE; XP002360796 & Can. J. Biochem., vol. 53, 1975, p. 920.

Database Beilstein, Beilstein Institut zur Förderung der Chemischen Wissenschaft, Frankfurt am, Main, DE; XP002360797 & Can. J. Chem., vol. 69, No. 5, 1991, pp. 772-778.

Database Beilstein, Beilstein Institut zur Förderung der Chemischen Wissenschaft, Frankfurt am, Main, DE; XP002360798 & Hoppe-Seyler'S Z. Physiol. Chem., vol. 52, 1907, p. 392.

Database Beilstein, Beilstein Institut zur Förderung der Chemischen Wissenschaft, Frankfurt am, Main, DE; XP002360799 & Tetrahedron Asymmetry, vol. 1, No. 12, 1990, pp. 861-864.

Database Beilstein, Beilstein Institut zur Förderung der Chemischen Wissenschaft, Frankfurt am, Main, DE; XP002360800 & Recl. Trav. Chim. PAYS-BAS, vol. 115, No. 7-8, 1996, pp. 353-356.

Database Beilstein, Beilstein Institut zur Förderung der Chemischen Wissenschaft, Frankfurt am, Main, DE; XP002360801 & J. Org. Chem., vol. 64, No. 14, 2000, pp. 5004-5009.

Database Beilstein, Beilstein Institut zur Förderung der Chemischen Wissenschaft, Frankfurt am, Main, DE; XP002360802 & J. Org. Chem., vol. 65, No. 15, 2000, pp. 4732-4735.

Database Beilstein, Beilstein Institut zur Förderung der Chemischen Wissenschaft, Frankfurt am, Main, DE; XP002360803 & Bioorg. Med. Chem. Lett., vol. 13, No. 10, 2003, pp. 1801-1804.

Database Beilstein, Beilstein Institut zur Förderung der Chemischen Wissenschaft, Frankfurt am, Main, DE; XP002360804 & Recl. Trav. Chim. PAYS-BAS, vol. 107, No. 3, 1998, pp. 242-247.

Database Beilstein, Beilstein Institut zur Förderung der Chemischen Wissenschaft, Frankfurt am, Main, DE; XP002360805 & J. Univ. Bombay Sci., vol. 6/2, 1937, pp. 116-119.

Database Beilstein, Beilstein Institut zur Förderung der Chemischen Wissenschaft, Frankfurt am, Main, DE; XP002360806 & J. Org. Chem., vol. 50, No. 25, 1985, pp. 5018-5022.

Database Beilstein, Beilstein Institut zur Förderung der Chemischen Wissenschaft, Frankfurt am, Main, DE; XP002360807 & J. Fluorine Chem., vol. 111, No. 2, 2001, pp. 153-160.

Database Beilstein, Beilstein Institut zur Förderung der Chemischen Wissenschaft, Frankfurt am, Main, DE; XP002360808 & Bull. Soc. Chim. Fr., vol. 134, No. 1, 1997, pp. 101-104.

Database Beilstein, Beilstein Institut zur Förderung der Chemischen Wissenschaft, Frankfurt am, Main, DE; XP002360809 & Tetrahedron Asymmetry, vol. 12, No. 7, 2001, pp. 971-974.

Database Beilstein, Beilstein Institut zur Förderung der Chemischen Wissenschaft, Frankfurt am, Main, DE; XP002360810 & Arch. Pharm., vol. 288, 1955, pp. 234-245.

Database Beilstein, Beilstein Institut zur Förderung der Chemischen Wissenschaft, Frankfurt am, Main, DE; XP002360811 & J. Med. Chem., vol. 30, No. 8, 1987, pp. 1321-1327.

Database Beilstein, Beilstein Institut zur Förderung der Chemischen Wissenschaft, Frankfurt am, Main, DE; XP002360812 & J. Am. Chem. Soc., vol. 5, 1984, pp. 1476-1480.

Database Beilstein, Beilstein Institut zur Förderung der Chemischen Wissenschaft, Frankfurt am, Main, DE; XP002360813 & Adv. Synth. Catal., vol. 343, No. 4, 2001, pp. 343-350.

Database Beilstein, Beilstein Institut zur Förderung der Chemischen Wissenschaft, Frankfurt am, Main, DE; XP002360814 & Bull. Chem Soc. Jpn., 43, 1970, pp. 3891-3894.

Database Beilstein, Beilstein Institut zur Förderung der Chemischen Wissenschaft, Frankfurt am, Main, DE; XP002360827 & Chem. Ber., vol. 55, 1922, p. 2365.

Database Beilstein, Beilstein Institut zur Förderung der Chemischen Wissenschaft, Frankfurt am, Main, DE; XP002360828 & Angew. Chem., vol. 116, No. 13, 2004, pp. 1707-1710.

Database Beilstein, Beilstein Institut zur Förderung der Chemischen Wissenschaft, Frankfurt am, Main, DE; XP002360829 & J. Org. Chem., vol. 65, No. 24, 2000, pp. 8381-8383.

Database Beilstein, Beilstein Institut zur Förderung der Chemischen Wissenschaft, Frankfurt am, Main, DE; XP002360830 & J. Chem. Soc., vol. 95, 1999, p. 557.

Database Beilstein, Beilstein Institut zur Förderung der Chemischen Wissenschaft, Frankfurt am, Main, DE; XP002360831 & Tetrahedron Lett., 1978, pp. 2243-2246.

Database Beilstein, Beilstein Institut zur Förderung der Chemischen Wissenschaft, Frankfurt am, Main, DE; XP002360832 & Org. Lett., vol. 5, No. 18, 2003, pp. 3169-3172.

Database Beilstein, Beilstein Institut zur Förderung der Chemischen Wissenschaft, Frankfurt am, Main, DE; P002360833 & Tetrahedron, vol. 57, No. 7, 2001, pp. 1277-1282.

Database Beilstein, Beilstein Institut zur Förderung der Chemischen Wissenschaft, Frankfurt am, Main, DE; XP002360834 & Tetrahedron, vol. 49, No. 26, 1993, pp. 5805-5816.

Database Beilstein, Beilstein Institut zur Förderung der Chemischen Wissenschaft, Frankfurt am, Main, DE; XP002360835 & Tetrahedron Asymmetry, vol. 4, No. 12, 1993, pp. 2411-2414.

Database Beilstein, Beilstein Institut zur Förderung der Chemischen Wissenschaft, Frankfurt am, Main, DE; XP002360836 & J. Med. Chem., vol. 36, No. 6, 1993, pp. 771-777.

Database Beilstein, Beilstein Institut zur Förderung der Chemischen Wissenschaft, Frankfurt am, Main, DE; XP002360837 & J. Agric. Food Chem., vol. 47, No. 1, 1999, pp. 190-201.

Database Beilstein, Beilstein Institut zur Förderung der Chemischen Wissenschaft, Frankfurt am, Main, DE; XP002360838 & Naunyn-Schmiedeberg'S Arch. Pharmacol., vol. 351, No. 5, 1995, pp. 491-499.

International Search Report mailed Mar. 3, 2006 in PCT/NL2005/000826.

HYDROXY-AROMATIC COMPOUND, PROCESS FOR THE PREPARATION THEREOF, AND USE OF THE COMPOUND

This application is the US national phase of international application PCT/NL2005/000826 filed 1 Dec. 2005 which designated the U.S. and claims benefit of EP 04078281.5 and EP 05075496.9, dated 2 Dec. 2004 and 1 Mar. 2005, respectively, the entire content of which is hereby incorporated by reference.

The invention relates to a hydroxy-aromatic compound.

Hydroxy-aromatic compounds as such are known, and are defined as compounds having an aromatic ring with at least one —OH group attached directly to it. An example of such a compound is phenol. Another example of such a compound is the known adduct of phenol and formaldehyde; this hydroxy-aromatic compound is used in the preparation of phenol-formaldehyde resins. These resins are known from for example A. Knop, L. A. Pilato, Phenolic Resins, Springer Verlag Berlin 1990. These resins have many known uses, such as for example the use of these resins in adhesives for the preparation of particle boards.

A disadvantage of the known hydroxy-aromatic compounds, and in particular of their formaldehyde adducts, is that their use is associated with health risks, relating to the emission of formaldehyde during resin preparation, resin curing and in end products.

It is the objective of the present invention to reduce or even eliminate the said disadvantage while still providing a compound suitable for the preparation of hydroxy-aromatic resins.

The objective is achieved in that the hydroxy-aromatic compound is a compound of formula (I)

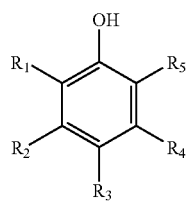

(I)

wherein:
at least one of the set consisting of $R_1$, $R_3$, and $R_5$ is a group of formula (II); any remaining one or two of the set consisting of $R_1$, $R_3$, and $R_5$ being H, OH, a $C_1$-$C_{12}$ alkyl group or an oligomeric or polymeric system;
$R_2$ and $R_4$ are H, OH, a $C_1$-$C_{12}$ alkyl group, or an oligomeric or polymeric system;
formula (II) is the following group:

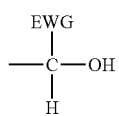

(II)

wherein EWG is an electron-withdrawing group.

The advantage of the compound according to the invention is that hydroxy-aromatic-based resins can be made that suffer less, or even not at all, from the health risks associated with the use of formaldehyde. Thus, resins prepared with the compound according to the present invention are in particular suitable for use in many applications such as adhesives, coatings, laminates, and shaped articles.

As is known in hydroxy-aromatic chemistry, the positions on the aromatic ring adjacent to and opposite the hydroxy group (i.e., ortho and para) have a different reactivity than the remaining two meta-positions. In formula (I), therefore, the groups $R_1$, $R_3$, and $R_5$ should be regarded within a similar context and are herein referred to as a set.

In the compound according to the invention, at least one of the groups in the set consisting of $R_1$, $R_3$, and $R_5$ is given by formula (II); the other one or two groups in the said set—in case not all three of the said set is given by formula (II)—is/are H, OH, or $C_1$-$C_{12}$ alkyl group, preferably H, OH, a $C_1$-$C_9$ alkyl group, or an oligomeric or polymeric system. If there are two groups not according to formula (II) then they may be the same or may be different. The oligomeric or polymeric system may be a hydroxy-aromatic resin, either of the resol or of the novolac type, preferably of the novolac type; or it may be a different type of thermosetting or thermoplastic system. Some examples of how the set according to the invention can be shaped are: $R_1$ is a group according to formula (II), $R_3$ is H, and $R_5$ is H; $R_1$ is a group according to formula (II), $R_3$ is H, and $R_5$ is $CH_3$; $R_1$ is H, $R_3$ is a group according to formula (II), and $R_5$ is H; $R_1$ and $R_3$ are a group according to formula (II), $R_5$ is H; $R_1$, $R_3$, and $R_5$ are all a group according to formula (II).

In the compound according to the invention, $R_2$ and $R_4$ are H, OH, a $C_1$-$C_{12}$ alkyl group, or an oligomeric or polymeric system; preferably $R_2$ and $R_4$ are H, OH or a $C_1$-$C_9$ alkyl group. $R_2$ and $R_4$ may be the same or may be different. Some preferred embodiments of $R_2$ and $R_4$ are: $R_2$ is OH and $R_4$ is H; $R_2$ is $CH_3$ and $R_4$ is H; $R_2$ is $CH_3$ and $R_4$ is $CH_3$; $R_2$ is H and $R_4$ is $C_4H_9$. $R_1$ and $R_2$ may be part of a multicyclic compound; the same holds mutatis mutandis for $R_2$ and $R_3$, $R_3$ and $R_4$, or $R_4$ and $R_5$.

The group according to formula (II) is an integral part of the compound according to the invention; it is either $R_1$, $R_3$, or $R_5$ in formula (I), or two of those, or all three. In formula (II), EWG is an electron-withdrawing group. EWG's are as such known to the skilled person. Examples of an EWG are acid-, ester-, cyano-, di-alkylacetal-, aldehyde-, substituted phenyl-, or trihalomethyl groups. Hydrogen is not an EWG. In a preferred embodiment, the group of formula (II) is a group according to formula (III):

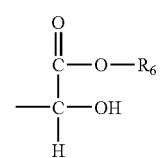

(III)

wherein $R_6$ is a $C_1$-$C_{12}$ alkyl group, aryl group, aralkyl group or cycloalkyl group. Preferably $R_6$ is a $C_1$-$C_{12}$ alkyl group; examples hereof are methyl, ethyl, propyl, butyl, pentyl, hexyl; more preferably, $R_6$ is a methyl group or an ethyl group.

In a preferred embodiment of the hydroxy-aromatic compound according to the invention, at least one of the set consisting of $R_1$, $R_3$, and $R_5$ is H. This has the advantage that the hydroxy-aromatic compound is better suitable for the preparation of the oligomeric or polymeric structures typical for hydroxy-aromatic resins. In another preferred embodiment, two of the set consisting of $R_1$, $R_3$, and $R_5$ are H. This has the advantage that such a hydroxy-aromatic compound can be used to create three-dimensional networks, an ability often desired in hydroxy-aromatic resins. The same ability of the hydroxy-aromatic compound to create three-dimensional networks is present in those embodiments where all of $R_1$, $R_3$, and $R_5$ are either H or a group according to formula (II).

The invention further relates to a process for the preparation of the hydroxy-aromatic compound as described above. The process according to the invention comprises a reaction step wherein a hydroxy-aromatic compound of formula (IV) is brought into contact with a compound according to formula (V), optionally in the presence of a catalyst, whereby formula (IV) is:

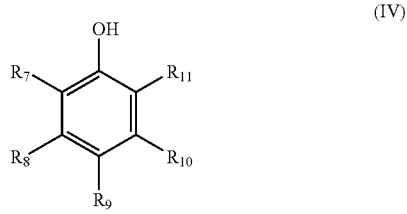

wherein $R_7$, $R_8$, $R_9$, $R_{10}$ and $R_{11}$ are H, OH, a $C_1$-$C_{12}$ alkyl group or an oligomeric or polymeric system, whereby at least one and preferably two or even three of the set consisting of $R_7$, $R_9$, and $R_{11}$ is or are H; and formula (V) is:

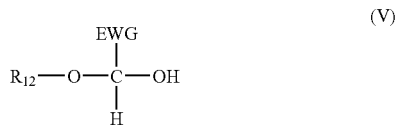

wherein EWH is an electron-withdrawing group and wherein $R_{12}$ is H, a $C_1$-$C_{12}$ alkyl group, aryl group, aralkyl group or cycloalkyl group.

Preferably, the compound according to formula (V) is an alkanol hemiacetal according to formula (VI):

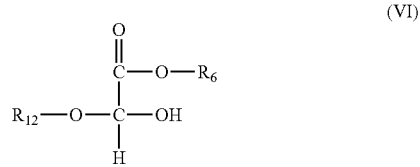

wherein $R_6$ is a $C_1$-$C_{12}$ alkyl group, aryl group, aralkyl group or cycloalkyl group and wherein $R_{12}$ is H, a $C_1$-$C_{12}$ alkyl group, aryl group, aralkyl group or cycloalkyl group. Preferably $R_6$ and $R_{12}$ are $C_1$-$C_{12}$ alkyl groups. Examples thereof are methyl, ethyl, propyl, butyl, pentyl, hexyl, and heptyl. $R_6$ and $R_{12}$ are in particular a methyl group or an ethyl group.

The process according to the invention comprises a reaction step. The purpose of the reaction step is to let a hydroxy-aromatic compound of formula (IV) react with a compound of formula (V). Thus these compounds must be brought together. The compound according to either formula (IV) or formula (V) may be one single compound or a mixture of two or more compounds falling within the scope of the formulas as defined above. Examples of preferred compounds according to formula (IV) are phenol, (2,3, or 4-)cresol, resorcinol, (2,3, or 4-)tert-butylphenol, (2,3, or 4-)nonylphenol, (2,3-2, 4-2,5-2,6 or 3,4-)dimethylphenol, (2,3, or 4-)ethylphenol, bisphenol A, bisphenol F, and hydrochinon. Examples of compounds according to formula (V), in particular of the preferred alkanol hemiacetals according to formula (VI), are methylglyoxylate methanol hemiacetal (GMHA™, DSM Fine Chemicals, Linz); ethylglyoxylate ethanol hemiacetal (GEHA™, DSM Fine Chemicals, Linz); ethylglyoxylate methanol hemiacetal; butylglyoxylate butanol hemiacetal; butylglyoxylate methanol hemiacetal; butylglyoxylate ethanol hemiacetal; isopropylglyoxylate isopropanol hemiacetal; propylglyoxylate propanol hemiacetal; cyclohexylglyoxylate methanol hemiacetal and 2-ethylhexylglyoxylate methanol hemiacetal. Further examples of compounds according to formula V are glyoxylic acid hydrate, methylglyoxylate hydrate and ethylglyoxylate hydrate.

It may be beneficial to execute the reaction step according to the invention in a solvent or dispersant. As solvents, those compounds are suitable in which the reactants dissolve sufficiently to let the reaction take place. Examples of such solvents are water and various organic solvents. Depending on the specific compound or compounds of formula (IV) and (V), it may well be possible to use one or more of the reactants as solvent; in such a case, it can be possible to forego on the use of a solvent that is essentially a non-reactant and to execute the reaction step in bulk. In particular, many of the compounds according to formula (V) and in particular according to formula (VI) are a liquid at temperatures between 10° C. and 100° C. and can act as dispersantisolvent as well as reactant.

Although the reaction step may proceed spontaneously once the respective compounds have been brought together, it may be useful to bring the compounds together in the presence of a catalyst in order to accelerate the reaction. As catalyst, preferably an acid or a base is used; in particular, a Lewis or a Brønsted type of acid is preferred—such as for example sulphuric acid—whereby the pH is reduced to between 0 and 5, preferably to between 1 and 4, in particular to between 2 and 3. Suitable examples of acid catalysts are sulphuric acid, nitric acid, hydrochloric acid, phosphoric acid, boric acid, tetrafluoroboric acid, paratoluene sulphonic acid, formic acid, ammonium sulphate, ammonium chloride, ammonium nitrate. Suitable examples of basic catalysts are ammonia, trimethyl amine, triethyl amine, DABCO (diazabicyclo-octane), DBU (diaza-bicyclo-undecene), DMAP (4-dimethylaminopyridine), sodium hydroxide, potassium hydroxide.

The temperature in the reaction step of present process can vary within wide limits, and preferably lies between 10° C. and 100° C. More preferably the process is carried out at between 40° C. and 90° C. The pressure in the present process preferably is between 0.005 MPa and 1.0 MPa, preferably between 0.02 MPa and 0.2 MPa; most preferably, the pressure is atmospheric.

As consequence of the reaction step, a compound according to formula (I) is formed; additionally, the compound $R_{12}OH$ is released as by-product. It may be desirable to isolate the compound according to formula (I); this may be achieved through techniques that are as such known, such as for example a combination of pH change, solvent exchange, evaporation and/or precipitation. If the compound according to formula (I) is not isolated, it may still be desirable to remove $R_{12}OH$; this may be achieved through techniques that are as such known, such as for example distillation. It may, however, also be acceptable or even desirable to let $R_{12}OH$ remain in the presence of the compound according to formula (I).

In the process for the preparation of the hydroxy-aromatic compound according to the invention, the molar ratio between the EWG-containing compound according to formula (V) (E) and the hydroxy-aromatic compound according to formula (IV) (H), herein referred to as E/H ratio, may vary between wide limits. Preferably, the E/H ratio lies between about 0.1 and about 10, more preferably between about 0.5 and about 3. If the E/H ratio is about 0.5 or lower, the resulting hydroxy-aromatic compound according to the invention can be a mixture having a significant amount of a compound according to formula (I) in which one of the set consisting of $R_1$, $R_3$, and $R_5$ is a group of formula (II). If the E/H ratio is about 3 or higher, the resulting hydroxy-aromatic compound according to the invention can be a mixture having a significant amount of a compound according to formula (I) in which all three of the set consisting of $R_1$, $R_3$, and $R_5$ are a group of formula (II). If the E/H ratio is about 1 or 2, the resulting hydroxy-aromatic compound according to the invention can be a mixture in which compounds according to formula (I) in which one, two or all three of the set consisting of $R_1$, $R_3$, and $R_5$ are a group of formula (II) are all clearly represented.

When executing the reaction step as described above, it was found that a further reaction can also be made to take place, namely the formation of a compound according to formula VII:

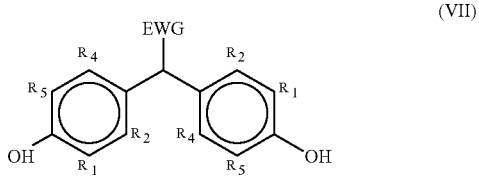

(VII)

In case the EWG is according to formula (VI), the compound according to (VII) will be as in formula (VIII):

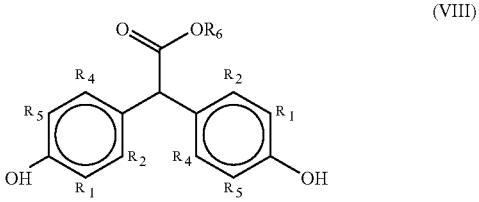

(VIII)

It was found that when executing the reaction step according to the invention, many hydroxy-aromatic compounds have a preference to first react on the para location of the aromatic moiety before doing so on the ortho location; hence the creation of compounds according to formula (VII) or (VIII). The present invention therefore also relates to compounds of formula (VII), in particular of formula (VIII), most preferably with $R_1$, $R_2$, $R_4$ and $R_5$ being all H and $R_6$ being methyl.

The compounds according to formula (VII) and (VIII) can typically be made by prolonged execution of the reaction step as described above for the preparation of compounds according to formula (I), whereby the E/H molar ratio preferably lies between 0.3 and 0.7, more preferably between 0.4 and 0.6.

The invention further relates to a process for the preparation of a hydroxy-aromatic resin. Such processes are as such known and comprise condensation reactions between a hydroxy-aromatic compound and a compound such as an aldehyde, and typically also subsequent condensation reactions; an example of such a process is the process for preparation of a phenol-formaldehyde resin. In the process according to the invention, a compound according to formula (I) is used in the (subsequent) condensation reactions. The (subsequent) condensation reactions may be executed in the same fashion and under similar conditions as described above for the preparation of the compound according to formula (I), (VII) and (VIII), although typically for a—further—prolonged period of time. The compound falling within the scope of formula (V) and in particular formula (VI) may be—aside from the hydroxy-aromatic compound according to formula (I) and/or the already formed oligomeric or polymeric structures—the sole other compound participating in the condensation reactions in the resin; it may also be possible to use other compounds such as aldehdyes like formaldehyde or furfural ($C_5H_4O_2$) in combination with the compound according to formula (V). Preferably, however, at least 5 or 10 mol. % of the compounds participating in the condensation reactions with a hydroxy-aromatic moiety in the resin are one or more compounds according to formula (V); more preferably, this is at least 20 or 30%; in particular, this is at least 40 or 50%; with strong preference, at least 60 or 70 mol. % of the compounds reacting with a hydroxy-aromatic moiety in the resin are one or more compounds according to formula (V); most preferably, this is at least 80 or 90% or even essentially 100%.

The resin comprises hydroxy-aromatic moieties (H) derived from hydroxy-aromatic compounds used as starting materials. The resin also comprises EWG-derived moieties and possibly aldehyde-derived moieties, together referred to as A. The resin thus has a molar A/H ratio. The molar A/H ratio in the resin preferably lies between 0.5 and 3, more preferably between 0.75 and 2. If the molar A/H ratio lies above 1, resol-type of resins can be formed whereby reactive 'A'-derived hydroxy groups are available. If the molar A/H ratio lies below 1, novolac-type of resins can be formed, in which essentially all 'A'-derived hydroxyl functionality has reacted away to form C—C and C—O ether bonds.

Resulting from the process as described above, the invention also relates to hydroxy-aromatic resins thus obtainable.

According to an embodiment of the invention, a hydroxy-aromatic resin can be prepared directly from raw materials comprising a compound according to formula (IV) as hydroxy-aromatic compound, and a compound according to formula (V). The conditions for achieving this are similar to those given above for the process or preparing the compound according to formula (I), and can be established by the skilled person via simple routine experimentation and using also his knowledge of the preparation of phenol-formaldehyde resins.

The invention moreover relates to the use of the hydroxy-aromatic aldehyde resin according to the invention for the preparation of coatings or shaped articles such as wood-based panels like particle boards and laminates, or mineral wool such as stone wool or glass wool. To this end, the resins may be used by methods and under conditions similar to those known per se from the use of known hydroxy-aromatic aldehyde resins like phenol-formaldehyde resins. A catalyst and other additives may be added to the resin before the resin is used for processing in its final application. Examples of customary additives are mould release agents, antistatic agents, adhesion promoters, plasticizers, colour enhancing agents, flame retardants, fillers, flow promoters, colorants, diluents, polymerization initiators, UV-stabilizers and heat stabilizers. Examples of fillers are glass fibres, mica, carbon fibres, metal fibres, clay, aramide fibres and strong polyethylene fibres.

The resin according to the invention may be used as such; however, it is also possible to subject the resin to a modification step; this is a reaction step designed to alter or enhance its functionality in a specific way. An example of an altered functionality is the solubility of the resin in water. An example of an enhanced functionality is the addition of a reactive group. An example of a modification step is to bring the resin in contact with compounds that react with the —OH groups; an example of such a compound is epichlorohydrin. Another example of a modification step is to bring the resin in contact with compounds that react with the —$OR_6$ groups; an example of such a compound is water; the hydrolysis of the —$OR_6$ group into a —COOH group increases the solubility of the resin in water. Also, the modification step may be achieved through a transesterification reaction between the —$OR_6$ groups and suitable compounds such as amines.

The present invention can be carried out in a variety of ways, as illustrated by the following non-limiting illustrative embodiments.

In a first illustrative embodiment, phenol and formaldehyde are used as raw materials to prepare—in a known fashion—a novolac-type of resin at a pH of 2. The phenol-formaldehyde novolac resin is then brought together with methylglyoxylate methanol hemiacetal (GMHA); this is done in an aqueous environment, at a temperature of about 80° C. and with an acidic catalyst at a pH of 2. The reaction is continued for 60-120 minutes, methanol being released and a resin according to the invention is formed. The resin according to the invention is then either used as adhesive in the production of a particle board or in the preparation of mineral wool, preferably with an acidic catalyst such as sulphuric acid added to the resin. For the production of particle board, dosing, press factors and other circumstances are normal (eg a temperature of about 140° C.). The resulting particle board will have a greatly reduced emission of formaldehyde compared to a particle board prepared by using only a standard phenol-formaldehyde resin. For the production of mineral wool such as stone wool, the resin is mixed with water so that a mixture having about 95-98 wt. % water content is formed, optionally aided by adding a base such as a metal hydroxide or amine or ammonia. This mixture is then sprayed on stone wool as it is just formed and has a temperature of about 1900° C. The mixture acts as coolant, and at the same time the resin is partially cured thereby substantially forming the end product; this all takes place in about 1 to 3 seconds. In an after-treatment with hot air of about 140-200° C. a fully cured product is obtained.

In a second illustrative embodiment, phenol and GMHA are brought together in an aqueous solution. The molar ratio between phenol and GMHA is 2:3. At an elevated temperature (about 80° C.) and at pH of 2 or lower, a resol-type of resin will be formed in about 60 minutes. Subsequently, the temperature is raised to about 150° C. and the mixture stirred at that temperature for about 3 hours to yield a stable resin. Afterwards, the resin is brought ready for use by adding an additional acid catalyst such as sulphuric acid. The resin is then used to prepare stone wool in the same fashion as in the previous illustrative embodiment.

In a third illustrative embodiment, cresol and GMHA are brought together in an aqueous solution. The molar ratio between cresol and GMHA is 4:3. Under conditions of elevated temperature (90° C.) and reduced pH (2), a novolac-type of resin will be formed. This resin can be converted into a water-born coating by adding a hardener such as adipic acid dihydrazide (ADH). If ADH is used as hardener, the coating will cure quickly (within 30 minutes) and at room temperature.

In a fourth illustrative embodiment, cresol and GMHA are brought together in an aqueous solution. The molar ratio between cresol and GMHA is 4:3. Under conditions of elevated temperature (90° C.) and reduced pH (2), a novolac-type of resin will be formed. The ester functionalities of the resin are then optionally saponified by raising the pH to 10. Subsequently, a reduction of pH to about 2 and evaporation of the water will yield a acid-functional solid resin. This resin is then mixed with an epoxy resin such as Epikote™ 828 (a liquid epoxy resin produced from bisphenol A and epichlorohydrin). The resulting mixture is then moulded and pressed to cure in the form of a shaped article.

Figure 2:
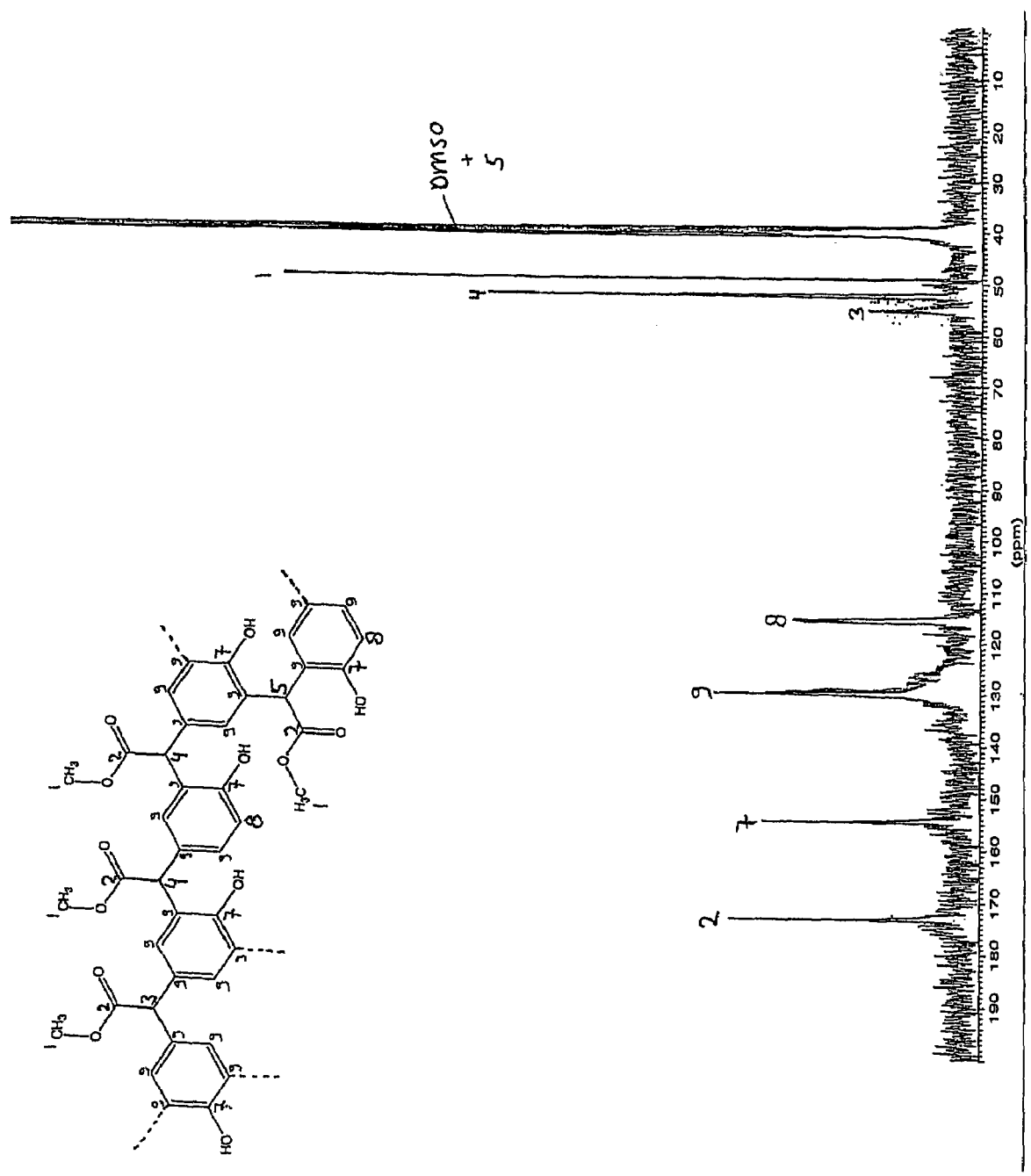

The present invention is illustrated with the following example, without being limited thereto, aided with FIGS. 1 and 2.

In the Figures, FIGS. 1 and 2 represent the results of NMR measurements as referred to in Example 1.

EXAMPLE 1

Under stirring, 313.7 gram of methylglyoxylate methanol hemiacetal (GMHA; 90 wt. % purity, 3 mol) and 190.1 gram of phenol (100% purity, 2 mol) were added to a 1 liter vessel at 23° C. and atmospheric pressure. The vessel was brought under nitrogen atmosphere to prevent phenolic-type discolorations as much as possible. The solid phenol dissolved in the liquid GMHA. Under stirring 5 ml of sulfuric acid of 85 wt. % was added drop-wise to the reaction mixture. The clear reaction mixture was heated to 100° C., and kept at 100° C. for 3 hours, During this reaction time, the viscosity of the resin (measured at room temperature) increased from 1 Pa·s. to 330 Pa·s. The reaction was then ended by cooling down the resin to room temperature. An NMR scan of the resin so obtained—dissolved in DMSO—is given in FIG. 1. Attention is drawn to the presence of peaks 3 and 6, evidencing a strong presence of para-only substituted phenol moieties, indicative of presence and/or resin-forming from compounds according to formula (VIII).

With the resin so obtained, two further tests were carried out: a reactivity test and a curing/solubility test.

In the reactivity test, a small amount of resin was put into a vessel and heated to 130° C. No catalysts or other compounds were added. A stirring rod was stuck into the resin, and with it the resin was continuously stirred until this was no longer possible due to the resin having reacted to such a stage that it became a lump/gel; this moment occurred within 10 minutes. The now partially cured resin was dissolved—with difficulty—in DMSO and an NMR spectrum was determined, see FIG. 2. In comparison with FIG. 1, peaks 3 and 6 have diminished or even disappeared. This means that para-only substituted phenol moieties were virtually absent; all these phenol moieties are still there but have also reacted on at least one ortho location.

In the solubility test, the resin was brought to 200° C. and kept at that temperature for 2 hours. No catalysts or other compounds were added. After 2 hours, the resin had cured into a hard, glassy material—this is indicative of significant to full curing, further confirmed by the fact that it was no longer possible to dissolve the material in DMSO. After cooling down the cured resin was crushed to small particles. Then, a mixture was made consisting of 5 grams of the crushed resin and 95 grams of water. This mixture was heated to 80° C. and kept at that temperature for 3 hours. After cooling down, the cured-resin particles were filtered from the mixture, dried at 120° C. and weighed. 96 wt. % or 4.80 grams of the resin was recovered.

The invention claimed is:

1. A resin comprising a hydroxy-aromatic compound of formula

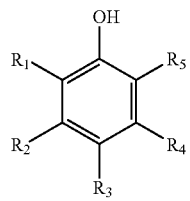

wherein:
at least one of the set consisting of $R_1$, $R_3$, and $R_5$ is a group of formula (III); any remaining one or two of the set consisting of $R_1$, $R_3$, and $R_5$ being H, OH, a $C_1$-$C_{12}$ alkyl group or an oligomeric or polymeric system;
$R_2$ and $R_4$ are H, OH, a $C_1$-$C_{12}$ alkyl group or an oligomeric or polymeric system; formula (III) is the following group:

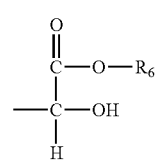

wherein $R_6$ is a $C_1$-$C_{12}$ alkyl group, aryl group, aralkyl group or cycloalkyl group.

2. A resin according to claim 1, wherein one or two of the set consisting of $R_1$, $R_3$, and $R_5$ is/are a group of formula (II) and wherein at least one of the said remaining one or two of the set consisting of $R_1$, $R_3$, and $R_5$ is H.

3. A resin comprising a hydroxy-aromatic compound of formula (VIII)

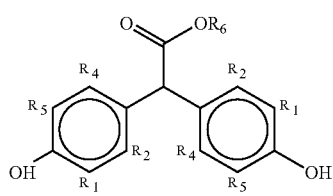

wherein $R_1$ and $R_5$ is a group of formula (III):

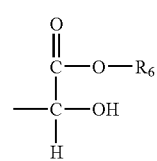

wherein $R_6$ is a $C_1$-$C_{12}$ alkyl group, aryl group, aralkyl group or cycloalkyl group; and wherein any remaining one of the set consisting of $R_1$ and $R_5$ being H, OH, a $C_1$-$C_{12}$ alkyl group or an oligomeric or polymeric system; and
wherein $R_2$ and $R_4$ are H, OH, a $C_1$-$C_{12}$ alkyl group or an oligomeric or polymeric system.

4. Process for the preparation of a resin comprising a reaction step which includes bringing a hydroxy-aromatic compound of formula (IV) into contact with an alkanol hemiacetal compound according to formula (VI), optionally in the presence of a catalyst, wherein formula (IV) is:

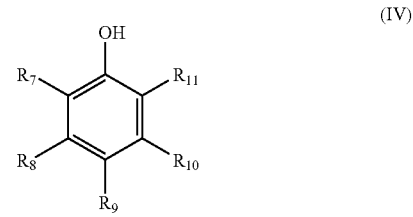

wherein $R_7$, $R_8$, $R_9$, $R_{10}$ and $R_{11}$ are H, OH, $C_1$-$C_{12}$ alkyl group, or an oligomeric or polymeric system, whereby at least one of the set consisting of $R_7$, $R_9$, and $R_{11}$ is H; and wherein formula (VI) is:

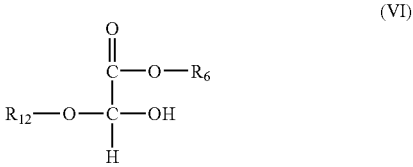

wherein $R_6$ is a $C_1$-$C_{12}$ alkyl group, aryl group, aralkyl group or cycloalkyl group; and
wherein $R_{12}$ is H, a $C_1$-$C_{12}$ alkyl group, an aryl group, an aralkyl group or a cycloalkyl group.

5. Process according to claim 4, wherein the hydroxy-aromatic compound of formula (IV) is brought into contact with the alkanol hemiacetal compound according to formula (VI) in the presence of an acid catalyst.

6. Process for the preparation of a hydroxy-aromatic resin, wherein a compound as described in claim 1 is used as a raw material.

7. Process for the preparation of a hydroxy-aromatic resin, wherein the raw materials comprise a compound according to formula(IV) as hydroxy-aromatic compound, and a compound according to formula (VI), wherein formula (IV) is:

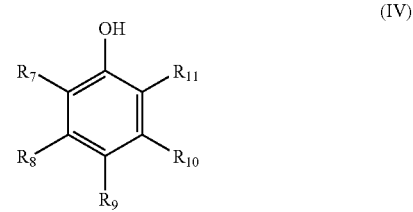

wherein $R_7$, $R_8$, $R_9$, $R_{10}$ and $R_{11}$ are H, OH, $C_1$-$C_{12}$ alkyl group, or an oligomeric or polymeric system, whereby at least one of the set consisting of $R_7$, $R_9$, and $R_{11}$ is H; and formula (VI) is an alkanol hemiacetal according to formula:

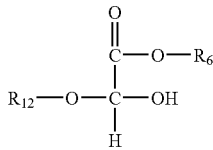
(VI)

wherein $R_6$ is a $C_1$-$C_{12}$ alkyl group, aryl group, aralkyl group or cycloalkyl group; and wherein $R_{12}$ is H, a $C_1$-$C_{12}$ alkyl group, an aryl group, an aralkyl group or a cycloakyl group.

8. Hydroxy-aromatic resin which is the reaction product of a hydroxy-aromatic compound according to formula (IV), and an alkanol hemiacetal compound according to formula (VI), wherein formula (IV) is:

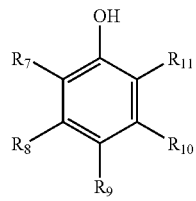
(IV)

wherein $R_7$, $R_8$, $R_9$, $R_{10}$ and $R_{11}$ are H, OH, $C_1$-$C_{12}$ alkyl group, or an oligomeric or polymeric system, whereby at least one of the set consisting of $R_7$, $R_9$, and $R_{11}$ is H; and wherein formula (VI) is:

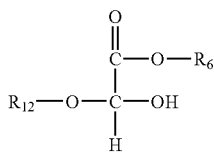
(VI)

wherein $R_6$ is a $C_1$-$C_{12}$ alkyl group, aryl group, aralkyl group or cycloalkyl group; and wherein $R_{12}$ is H, a $C_1$-$C_{12}$ alkyl group, an aryl group, an aralkyl group or a cycloakyl group.

9. A coating comprising a hydroxy-aromatic resin according to claim 8.

10. A coating comprising a hydroxy-aromatic resin according to claim 8.

11. A shaped article selected from the group consisting of wood-based panels and mineral wool, in which the shaped article comprises a hydroxy-aromatic resin according to claim 8.

\* \* \* \* \*